US 7,515,265 B2

(12) United States Patent
Alfano et al.

(10) Patent No.: US 7,515,265 B2
(45) Date of Patent: Apr. 7, 2009

(54) IMAGING SYSTEMS AND METHODS TO IMPROVE BACKSCATTERING IMAGING USING CIRCULAR POLARIZATION MEMORY

(75) Inventors: Robert R. Alfano, Riverdale, NY (US); Xiaohui Ni, New York, NY (US)

(73) Assignee: Research Foundation of the City University of New York, New York, NY (US)

( * ) Notice: Subject to any disclaimer, the term of this patent is extended or adjusted under 35 U.S.C. 154(b) by 314 days.

(21) Appl. No.: 11/414,738

(22) Filed: Apr. 27, 2006

(65) Prior Publication Data

US 2007/0016080 A1 Jan. 18, 2007

Related U.S. Application Data

(60) Provisional application No. 60/675,479, filed on Apr. 28, 2005.

(51) Int. Cl.
*G01J 4/00* (2006.01)
*G01N 33/48* (2006.01)

(52) U.S. Cl. ........................ 356/364; 356/36; 356/368; 356/369; 356/73; 356/39; 600/342; 600/310; 600/332; 600/160

(58) Field of Classification Search .................... 356/39, 356/73, 364–369; 600/342, 310, 325, 332, 600/160; 606/14, 15

See application file for complete search history.

(56) References Cited

U.S. PATENT DOCUMENTS

| 4,717,252 A | 1/1988 | Halldorsson et al. |
| 5,219,345 A | 6/1993 | Potter |
| 5,371,368 A | 12/1994 | Alfano et al. |
| 5,847,394 A | 12/1998 | Alfano et al. |
| 5,990,996 A | 11/1999 | Sharp |
| 6,005,916 A | 12/1999 | Johnson et al. |
| 6,011,626 A | 1/2000 | Hielscher et al. |
| 6,208,886 B1 | 3/2001 | Alfano et al. |

(Continued)

OTHER PUBLICATIONS

Wang, et al., "Ballistic 2-D Imaging Through Scattering Wall Using an Ultrafast Kerr Gate", Science 253, 769(1991).

(Continued)

*Primary Examiner*—L. G Lauchman
(74) *Attorney, Agent, or Firm*—Darby & Darby

(57) ABSTRACT

An optical technique to improve the imaging of a target inside suspensions of scattering particles includes the illumination of the scattering particles with circularly polarized light. The backscattered light from the host medium preserves the helicity of incident light, while the backscattered light reflected from the target is predominated with light of opposite helicity. Based on the observed helicity difference in the emerging light that originated at the target and that backscattered from the medium, the present optical technique improves the image contrast using circular polarization. This approach makes use of polarization memory which leads to the reflected light from the target accompanied by weak diffusive backscattered light. Using the present technique, improved imaging of the artery wall is achieved and plaque composition can be assessed through a blood field associated with the artery. The scattering from the particles, such as red blood cells, in the blood is reduced due to polarization memory. The present invention can be also applied to other biomedical application, as well as image targets through adverse environmental conditions, such as fog, clouds, smoke, murky water, etc.

39 Claims, 7 Drawing Sheets

U.S. PATENT DOCUMENTS

| | | | |
|---|---|---|---|
| 6,624,890 B2* | 9/2003 | Backman et al. | 356/369 |
| 7,149,567 B2* | 12/2006 | Demos et al. | 600/473 |
| 2004/0151626 A1 | 8/2004 | Cunningham et al. | |

OTHER PUBLICATIONS

Huang, et al., "Optical Coherent Tomography", Science 254, 1178(1991).

Yoo, et al., "Time-Resolved Coherent and Incoherent Components of Forward Light Scattering in Random Media." Opt. Lett. 15, 320(1990).

O'Leary, et al, "Experimental Images of Heterogeneous Turbid Media by Frequency-Domain Diffusing-Photon Tomography", Opt. Lett. 20, 426(1995).

Guo, et al.; Proc. Natl. Acad. Sci. 96, 10854 (1999).

Schmidt, et al., "Imaging Through Random Media by Use of Low-Coherence Optical Heterodyning", Opt. Lett. 20, 404(1995).

Dolne, et al., "IR Fourier Space Gate and Absorption Iimaging through Random Media", Lasers in the life Sci. 6, 131(1994).

Masters, et al, "Ultraviolet Confocal Fluorescence Microscopy of the In Vitro Cornea: Redox Metabolic Imaging", Appl. Opt. 32, 592(1993).

Demos, et al. "Optical Polarization Imaging." Appl. Opt. 36, 150 (1997).

Lewis, et al, "Backscattering Target Detection in a Turbid Medium by Polarization Discrimination," Appl. Opt. 38, 3937 (1999).

Pernicka, et al, "Improvement of Underwater Visibility by Reduction of Backscatter with a Circular Polarization Technique," Appl. Opt. 6, 741 (1967).

* cited by examiner

IMAGING SYSTEMS AND METHODS TO IMPROVE BACKSCATTERING IMAGING USING CIRCULAR POLARIZATION MEMORY

CROSS-REFERENCE TO RELATED APPLICATION

The present application claims the benefit of U.S. patent application Ser. No. 60/675,479, filed Apr. 28, 2005, which is hereby expressly incorporated herein in its entirety.

TECHNICAL FIELD

The present invention is directed to imaging techniques and systems to improve the image contrast of a target inside adverse turbid conditions, such as blood flow, surgical smoke, fog, clouds, murky water, etc.

BACKGROUND

In the United States alone, more than 650,000 people die each year of heart attacks related to coronary artery disease due to plaque build-up on the inside walls of the arteries. Various diagnostic methods have been developed to characterize and image coronary plaques in the vessel wall. These methods include angioscopic imaging, intracoronary coronary ultrasound (ICUS), and magnetic resonance imaging (MRI). Each of these methods exhibits some relative strengths and limitations/deficiencies. Optical imaging represents a promising new technology for imaging the vulnerable plaque with a level of resolution not previously achieved with the use of above conventional imaging modalities. Optical imaging can be performed with a catheter integrated with a relatively inexpensive optical fiber. A major challenge of optical imaging is that the scattering effect from the blood, especially from the red blood cells with an average diameter of 7.65 µm, blurs the image quality of the artery surface and subsurface. The absorption is small in the near infrared region from 0.8 µm to about 1.4 µm.

The use of laser surgery and advancements therein have rapidly increased in the recent years. However, laser surgery and laser cauterizing tissue normally is accompanied by the unwanted production of a cloud of smoke and vaporized particles which tend to obscure the target area (e.g., tissue).

There is thus a perceived need to develop a technique to overcome the resulting optical scattering effect in order to see through the surgical smoke and observe the target since an accurate target image is many times not possible to obtain using conventional imaging techniques.

In particular, there are many other situations in which the detection of an object present in a turbid, i.e., highly scattering, medium is highly desirable. For instance, the detection of a tumor embedded within tissue is one such example where detection of the tumor using optical imaging is difficult due to the surrounding environment that includes tissue and blood. Although X-ray techniques provide some measure of success in detecting objects in a turbid medium, they are typically not well-suited for detecting very small objects, e.g., tumors less than 1 mm in size embedded in tissue or for detecting objects in a thick or concentrated medium. In addition, X-ray radiation can present safety hazards to a person exposed thereto and thus, it would be desirable to find an alternative procedure. Ultrasound and magnetic resonance imaging (MRI) offer alternatives to the use of X-rays but have their own drawbacks and thus, all of the foregoing techniques have a number of associated deficiencies and all are particularly not well suited for a turbid medium environment.

Accordingly, it can be readily appreciated that there is an outstanding need for a high resolution optical imaging technique that is adapted for use in imaging an object in a turbid medium. Degradation of the scattering effect on non-invasive medical imaging, as well as signal transmission through atmospheric environments, are significant problems that limit the use of optical imaging techniques and the ability to obtain high resolution images.

Light propagating through a turbid medium undergoes multiple scattering, which randomizes the direction of propagation, phase, and polarization of the incident light. The image quality is degraded in this process and therefore, the resulting image is of poor quality and resolution. To reduce the effect of multiple scattering on obscuring the image, over the years various techniques have been introduced, such as time-resolved techniques, ballistic 2-D imaging through scattering wall using an ultrafast Kerr gate, optical coherent tomography, time-resolved coherent and incoherent components of forward light scattering in random media, frequency-domain techniques, nonlinear optical techniques, subsurface tumor progression investigated by noninvasive optical second harmonic tomography, optical low-coherence, Fourier space gate technique, and confocal fluorescence microscopy.

Details of the above types of techniques and systems can be found in following patents and articles: U.S. Pat. No. 5,371,368, issued Dec. 6, 1994 to Alfano et. al.; Wang, et al, Ballistic 2-D imaging through scattering wall using an ultrafast Kerr gate, Science 253, 769(1991); Huang, et al, Optical coherent tomography, Science 254, 1178(1991); Yoo, et al, Time-resolved coherent and incoherent components of forward light scattering in random media, Opt. Lett. 15, 320(1990); O'Leary, et al, Experimental images of heterogeneous turbid media by frequency-domain diffusing-photon tomography, Opt. Lett. 20, 426(1995); U.S. Pat. No. 6,208,886, issued Mar. 27, 2001 to Alfano et. al.; Guo, et al.; Proc. Natl. Acad. Sci. 96, 10854 (1999); Schmidt, et al, Imaging through random media by use of low-coherence optical heterodyning, Opt. Lett. 20, 404(1995); Dolne, et al, IR Fourier space gate and absorption imaging through random media, Lasers in the life Sci. 6, 131(1994); and Masters, et al, Ultraviolet confocal fluorescence microscopy of the in vitro cornea: redox metabolic imaging, Appl. Opt. 32, 592(1993), all of which are hereby incorporated by reference in their entireties.

However, the above techniques are limited by small imaging depth and the techniques are difficult to implement due to the sophisticated mathematical problems that are encountered in implementation or due to complicated experimental setups, etc. and some polarization imaging techniques have been developed and can be adapted for use in the present invention, See e.g., U.S. Pat. No. 5,847,394, issued Dec. 8, 1998 to Alfano et al; Demos, et al.; Optical polarization imaging, Appl. Opt. 36, 150 (1997); Lewis, et al, Backscattering target detection in a turbid medium by polarization discrimination, Appl. Opt. 38, 3937 (1999); and Pernicka, et al, Improvement of underwater visibility by reduction of backscatter with a circular polarization technique, Appl. Opt. 6, 741 (1967), all of which are incorporated herein by reference in their entireties.

SUMMARY

The present invention is directed to an imaging system and imaging method that utilize a polarization memory effect in backscattering temporal profiles and imaging profiles of a target contained in a turbid medium. When circularly polarized light impinges on large particle suspensions of the host turbid medium, the backscattered light from the target inside the turbid medium is dominated with light of opposite helicity and forms the imaging information. In contrast, the backscattered light from the large particle suspensions has the same helicity of the incident light and therefore is considered as background noise to the imaging information.

According to one embodiment of the present invention, a target inside a turbid medium formed with large particle suspensions is illuminated with circularly polarized light. By selecting out the backscattered light with opposite helicity (which represents main target information accompanied by low background light), the image contrast is significantly improved in comparison to imaging based on a linear polarization technique. This combination of circular polarization states permits an instrument of the system to be used for diverse applications, such as imaging through biological tissues and atmospheric environments in which the wavelength is less than the size of the scattering particles ($\lambda < a$).

The present invention is also directed to imaging systems and devices that employ the above imaging method for producing improved, high resolution images of an object located in a turbid medium. For example, the present invention is directed to applications of analyzing coronary lesions, such as vulnerable plaque through blood in an artery, as well as applications where imaging of a target is performed through surgical smoke and other turbid conditions/environments.

Additional objects, features, aspects and advantages of the present invention will be set forth in part in the description which follows, and in part will be obvious from the description or may be learned by practice of the invention. Various embodiments of the invention will be described in sufficient detail to enable those skilled in the art to practice the invention, and it is to be understood that other embodiments may be utilized and that changes may be made without departing from the scope of the invention. The following detailed description is, therefore, not to be taken in a limiting sense, and the scope of the present invention is best defined by the appended claims.

BRIEF DESCRIPTION OF THE DRAWING FIGURES

The inventive system and method will now be described with reference to the annexed drawings, in which:

FIGS. 2a and 2b are time-resolved profiles for copolarized (solid) and cross-polarized (dashed curve) backscattered light from the turbid medium of FIG. 1 that contains large particles, in which FIG. 2a shows a sample illuminated with linearly polarized light and FIG. 2b shows illumination with left-handed circularly polarized light;

Figure 4A:
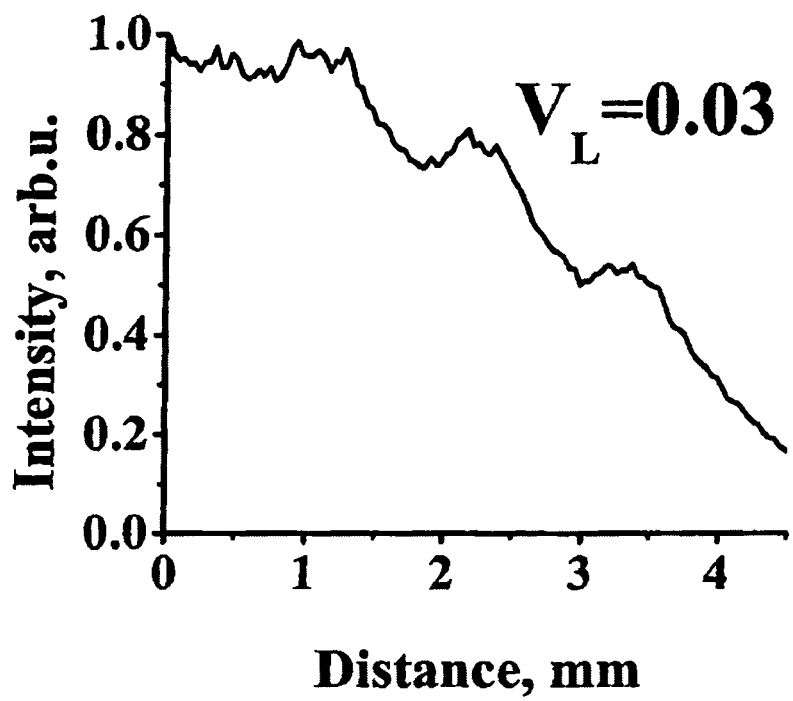
Figure 4B:
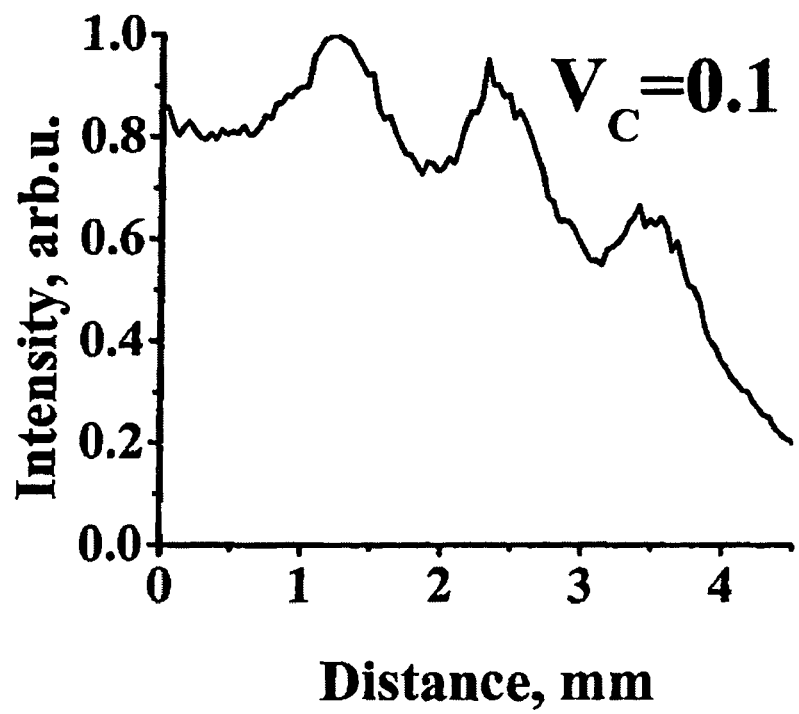
Figure 5:
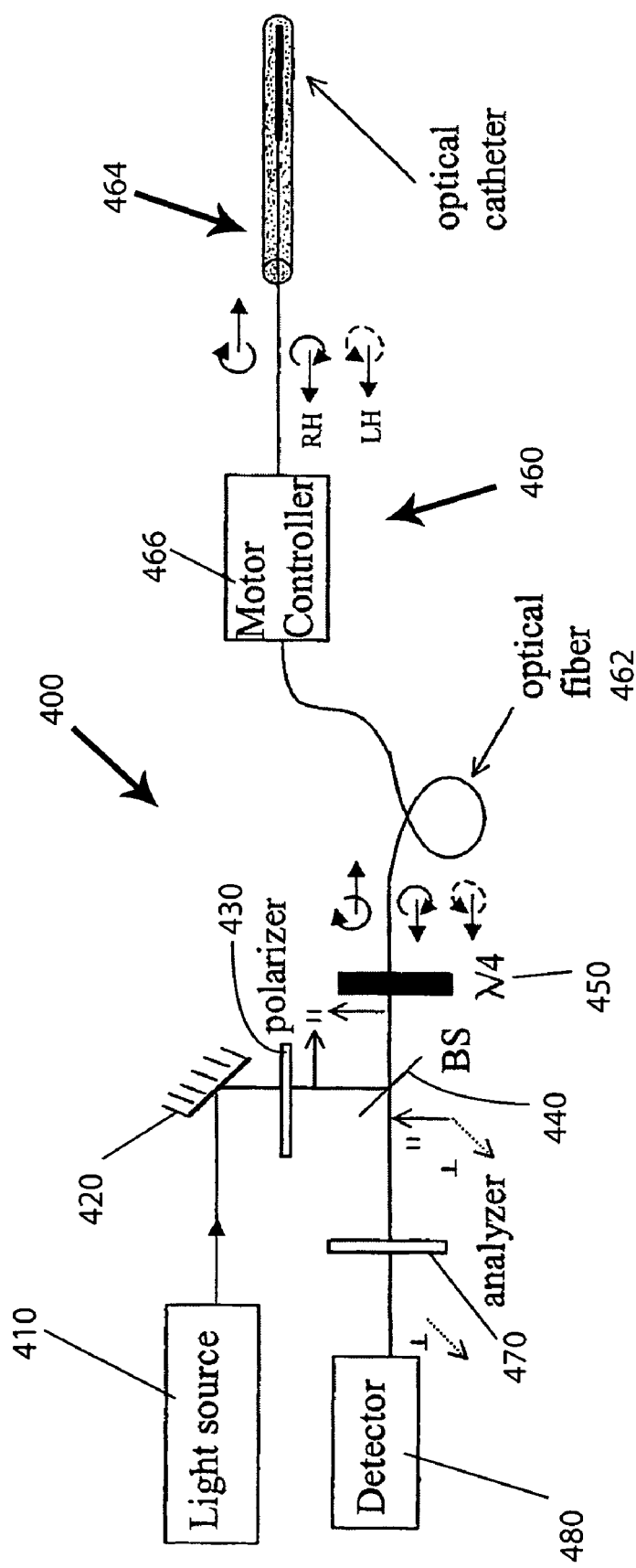
Figure 6:
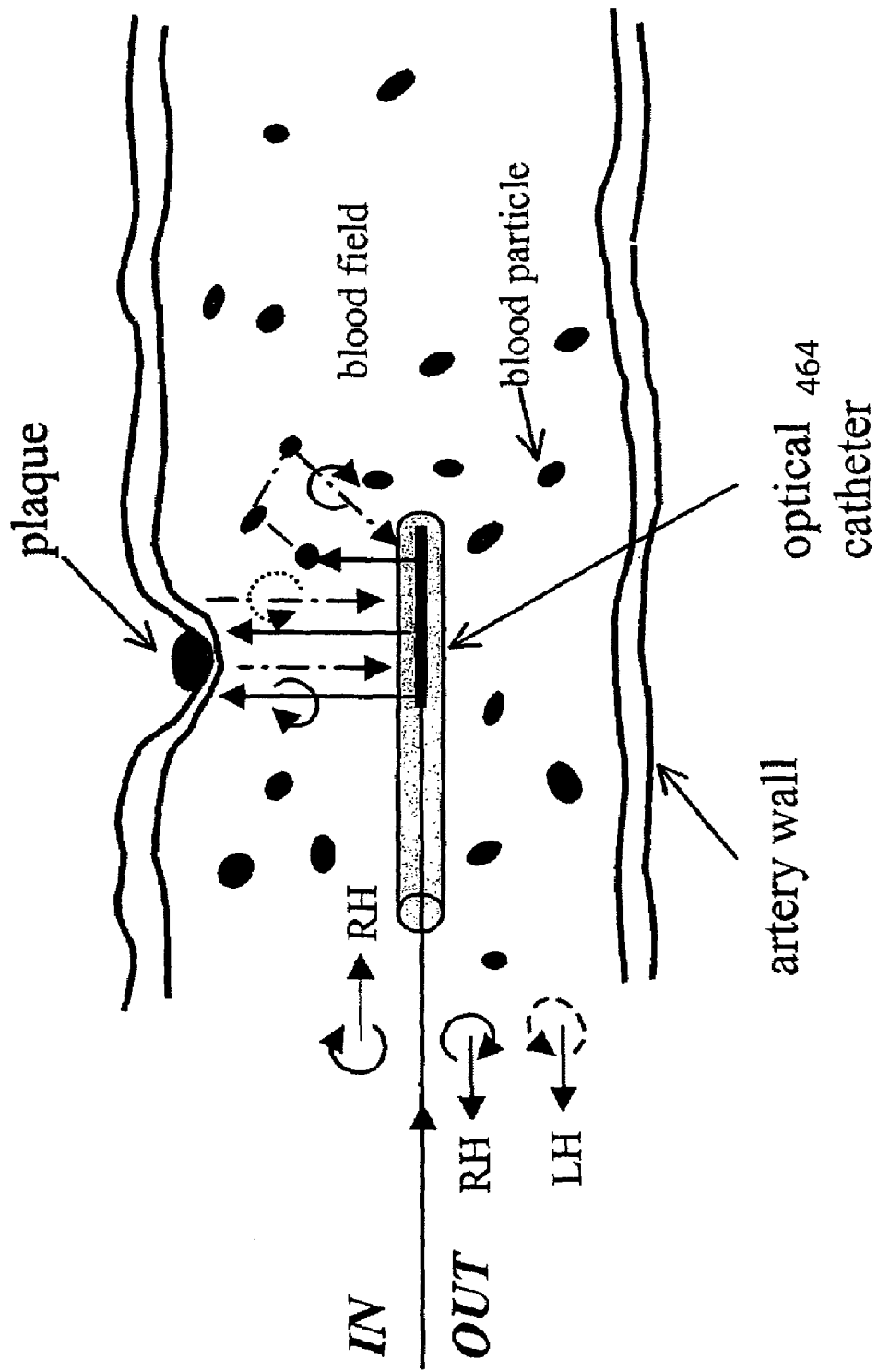
Figure 7:
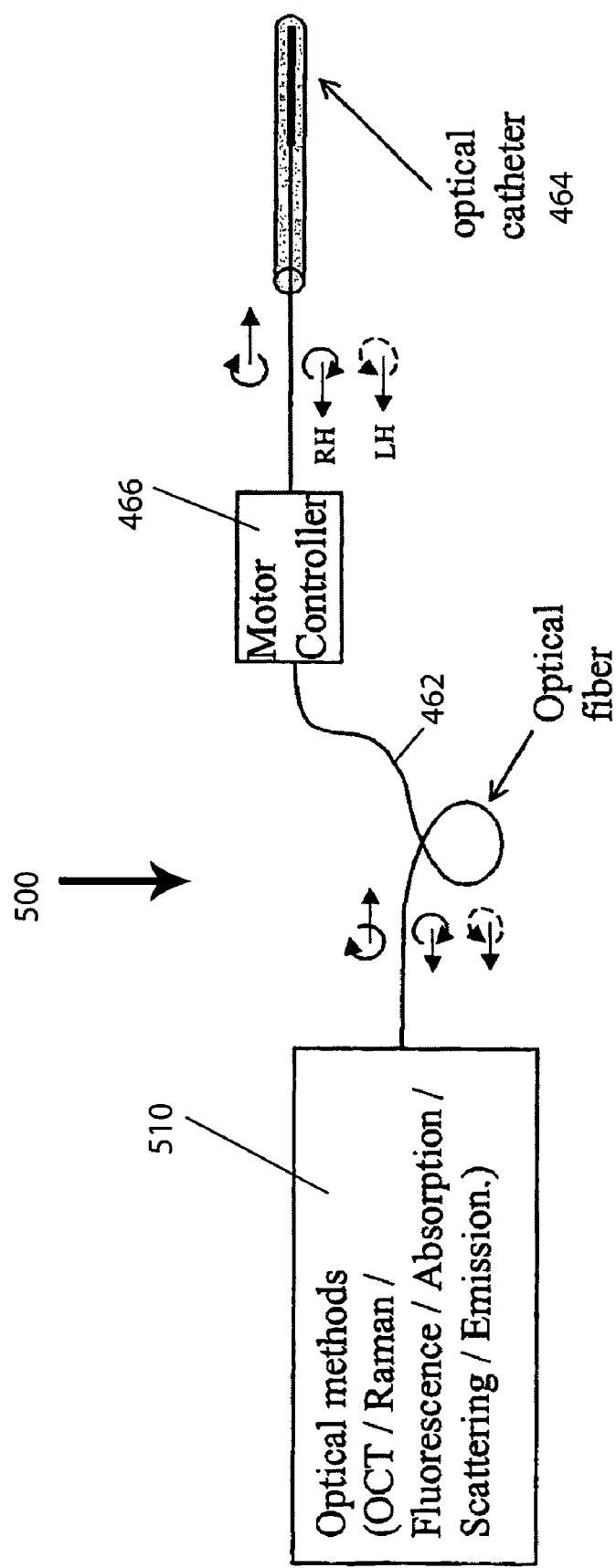

FIGS. 4a and 4b intensities profiles of a high reflective target inside a turbid medium containing large particles, where FIG. 4a shows imaging with linearly copolarized light and FIG. 4b shows imaging with circularly cross-polarized light;

FIG. 5 is a schematic view of an intravascular imaging system according to one exemplary embodiment of the present invention;

FIG. 6 is an enlarged cross-sectional view of light migration inside an artery when a device illuminates the artery wall through the blood field; and FIG. 7 is a schematic diagram of a system for imaging the artery wall using circular polarization memory combined with other imaging methods.

DETAILED DESCRIPTION OF PREFERRED EMBODIMENTS

The present invention is directed to a method or technique, as well as an imaging arrangement or system, which can improve the quality of image of an object that is obscured inside a highly scattering medium, such as a turbid medium, that consists of randomly distributed particles. As a result of the turbid medium, prevalent backscattering results when an object inside the turbid medium is illuminate. If the backscattered light is not depolarized, one anticipates that it will consist mainly of the circularly polarization state corresponding to that which would result from specular reflection by a perfectly conducting plate. However, this intuition is correct only for particles in the medium whose sizes are smaller than the wavelength. For larger particles in the medium, the opposite is true. The unexpected memory of the incident circular polarization is called polarization memory. As used herein and according to one aspect of the present invention, "large particles" and "large particle suspensions" refer to particles that have a dimension, such as diameter, that is greater than a wavelength ($\lambda$) of the backscattered light.

The imaging technique according to the present invention is based on the polarization memory of circularly polarized light from the turbid medium. When linearly polarized light enters a turbid medium, the backscattered light from the turbid medium (e.g., particles) and from the target is composed predominately of polarized light that is parallel to incident polarization. However, a polarization technique that utilizes linearly polarized light, which improves the image by cutting the diffuisively backscattered light with perpendicular polarization, has only limited improvement since a significant portion of backscattered light from the medium has the same polarization as the signal from the target.

Alternatively, imaging with circularly polarized light from a turbid medium formed of small particle suspensions offers only limited improvement compared to using linearly polarized light since the backscattered light from both the reflective target and the medium is predominated by helicity flipped light. In contrast, for suspensions of large particles, the helicity of backscattered light from the medium is mainly the same helicity as the incident circular polarization due to polarization memory. The polarization memory effect that is observed from large particle suspensions demonstrates that such technique improves the image contrast of a target.

Figure 1:
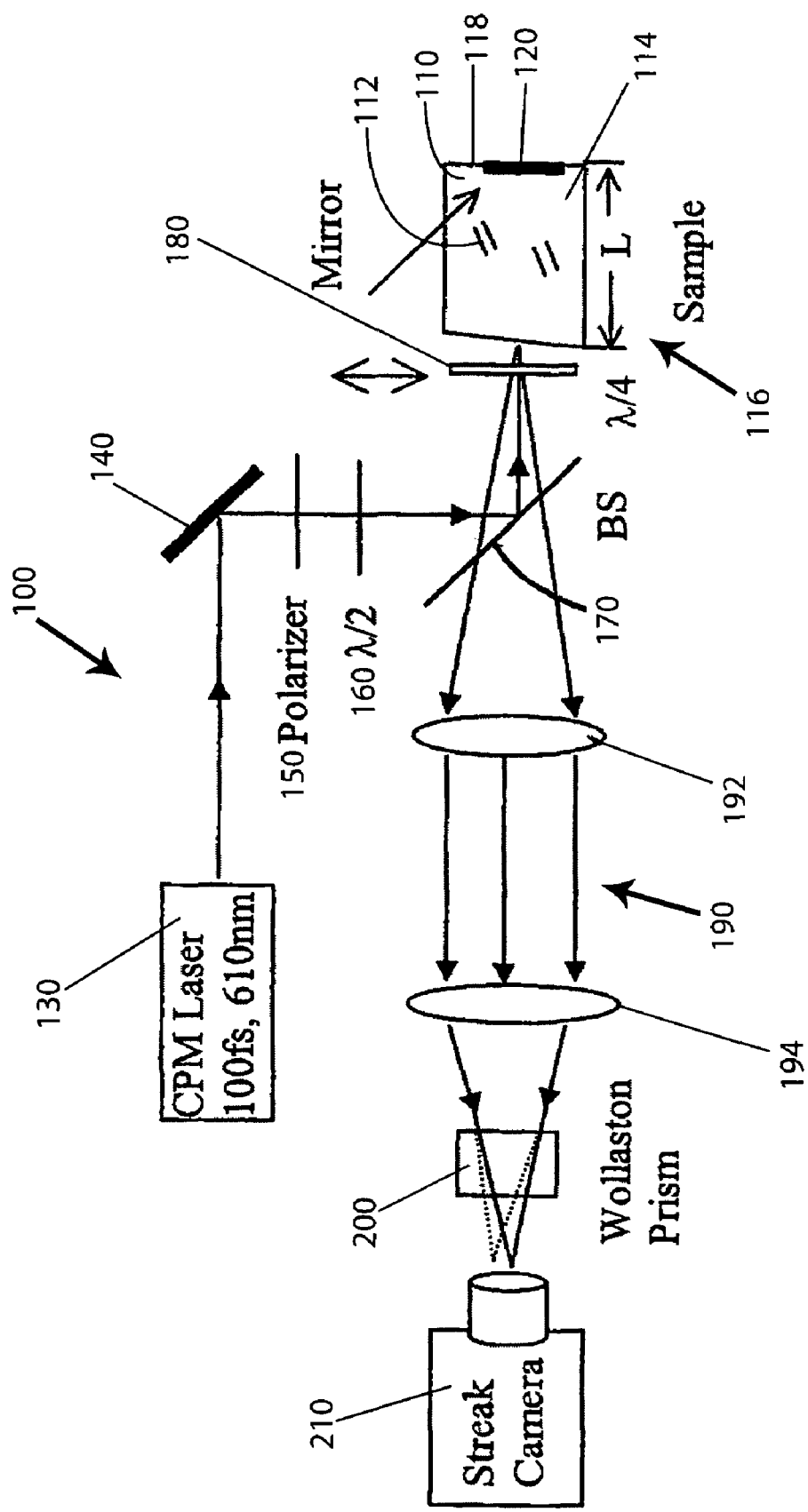
FIG. 1 is a schematic diagram of an arrangement to illustrate a polarization memory effect for an object in a turbid medium according to one aspect of the present invention.

FIG. 1 illustrates an arrangement 100 that illustrates a circular polarization memory that is observed with respect to detection of a target in a turbid medium 110 according to aspect of the present invention. A turbid medium sample 110 is provided and is in the form of particles 112 (in this case, polystyrene particles) (refractive index n=1.59) suspended inside deionized water 114 to illustrate the polarization memory effect when the sample is illuminated with circular polarized light as described below. The particles 112 and water 114 are contained within a cell 116 or any other type of suitable structure. A mirror 120 is placed inside the cell 116 on a back wall 118 thereof to act as a target object.

A source 130 of light is provided for illuminating the target in the turbid medium 110. According to one exemplary embodiment, the source 130 is in the form of a laser or the like that generates laser pulses that are directed toward the turbid medium 110 as illustrated in FIG. 1. For example, the source 130 can be in the form of a laser that generates ultrafast laser pulses of 100 fs. The laser pulses contact a first mirror 140 that changes the direction of the laser pulses (light) and in particular, the mirror 140 directs the light first to a polarizer 150 and then to a half-wave plate 160 to ensure the linear polarization of the laser pulses that are to be inputted into the turbid medium 110 for illumination of a target therein.

After passing through the polarizer 150 and the half-wave plate 160, the light (i.e., laser pulses) contacts a beam splitter 170 that changes the path of the light and directs the light toward the sample, which in this case is the turbid medium 110 formed of the particles 112 and the water 114. Between the beam splitter 170 and the sample of turbid medium 110, a quarter-wave plate 180 is provided and preferably is movably positioned relative to the turbid medium 110 so as to permit the quarter-wave plate 180 to be moved relative to the turbid medium 110.

When the quarter-wave plate 180 is positioned before the sample (turbid medium 110), the incident linear polarized light that is created by the polarizer 150 is changed to circularly polarized light to impinge the sample (turbid medium 110). A half-wave plate 160 is provided to rotate the direction of the linear polarization and functions to provide convenient adjustment of the polarized light.

The impingement of the sample by the polarized light causes backscattered light to be generated due to the make-up of the turbid medium 110, etc. The backscattered light passes through the quarter-wave plate 180 again and turns back into linear polarized light. Without the quarter-wave plate 180 in the position illustrated in FIG. 1, linear polarized light would form the basis for taking measurements with respect to the quality of imaging since the quarter-wave plate 180 serves to convert circular polarized light into linear polarized light.

After the backscattered light passes through the quarter-wave plate 180, the backscattered light passes through an optical arrangement 190, for example, a first optic element 192 (e.g., a first lens) and a second optic element 194 (e.g., a second lens) that serve to deliver the backscattered light to a prism 200. The backscattered light is then passed through a member that is configured to separate the co-polarized light from the cross-polarized light. For example, one suitable member is a prism 200 (e.g., a Wollaston prism) that is used to separate the copolarized backscattered light (parallel to incident polarization or of same helicity) and the cross-polarized backscattered light (perpendicular to incident polarization or of opposite helicity).

According to one embodiment and for a circular polarization measurement, left-handed circularly polarized light is incident on the sample (turbid medium 110); however, the opposite is equally possible in that right-handed circularly polarized light can be the incident light. After passing through the prism 200, the backscattered light is introduced to a detector 210 or the like. The detector 210 can be in the form of a photodetector that is capable of processing the received information (signals) and recording a time-resolved intensity profile of the backscattered light that is observed from the illumination of the target in the turbid medium. As is know, a photodetector is generally a transducer that is capable of accepting an optical signal and producing an electrical signal containing the same information as in the optical signal. The information can then be displayed in any number of different ways, including the intensity profiles of FIGS. 2a and 2b. There are a number of different types of photodetectors and the selection of which will depend upon a number of different factors including the specification application details and what type of information is desired for recording.

It will further be appreciated that the term "detector" as used herein refers not only to photodetectors that function in the above manner in that they accept an optical signal and produce an electrical signal that can then be displayed as an intensity profile or the like but also, the term "detector" refers to other types of detectors that are capable of recording images. For example, one type of detecting device (detector) that is capable of recording images is a charge-coupled device (CCD) which is special type of detector. In particular, a charge-coupled device (CCD) is a sensor for recording images and consists of an integrated circuit containing an array of linked, or coupled, capacitors. Under the control of an external circuit, each capacitor can transfer its electrical charge to one or another of the neighboring capacitors. A CCD is typically configured in a system such that an image is projected by a lens or the like on the capacitor array, causing each capacitor to accumulate an electric charge proportional to the light intensity at that location. A one-dimensional array, used in line-scan cameras, captures a single slice of the image, while a two-dimensional array, used in video and still cameras, captures the whole image or a rectangular portion of it. Once the array has been exposed to the image, a control circuit causes each capacitor to transfer its contents to its neighbor. The last capacitor in the array dumps its charge into an amplifier that converts the charge into a voltage. By repeating this process, the control circuit converts the entire contents of the array to a varying voltage, which it samples, digitizes and stores in memory. Stored images can be transferred to a printer, storage device or video display.

In FIG. 1, the detector is the form of a photodetector for recording an intensity profile over time of the backscattered light and more specifically, is in the form of a camera (Hamamatsu 2 ps streak camera) 210 that records the time-resolved profiles of the backscattered light.

Figure 2A:
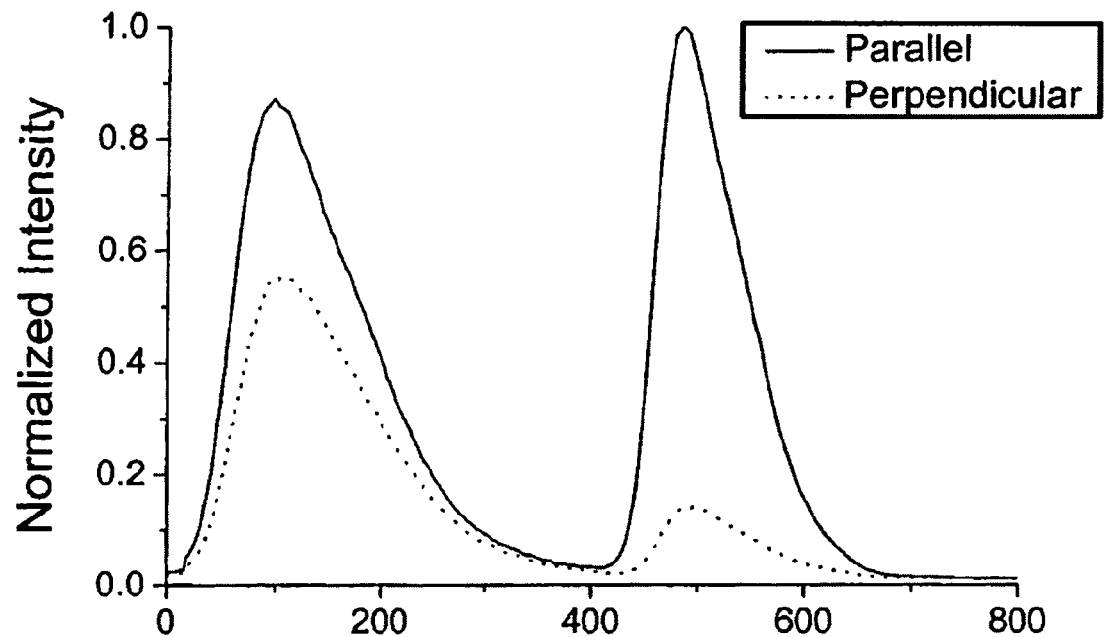
Figure 2B:
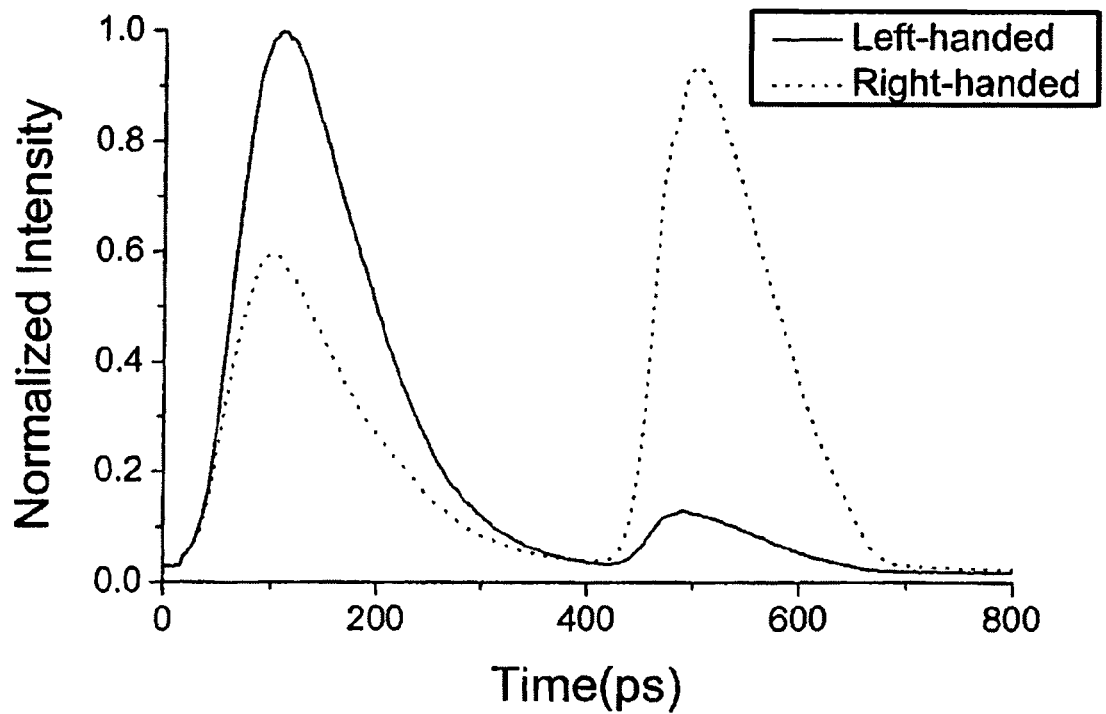

FIG. 2 shows backscattering profiles of light from a turbid medium containing large particles that have a diameter a=8 μm and a scattering coefficient $\mu_s$=1.54 cm$^{-1}$. The sample is illuminated with linearly polarized light which produces the backscattering profiles (intensity profiles) illustrated in FIG. 2(a) and is also illuminated with left-handed circularly polarized light which produces the backscattering profiles illustrated in FIG. 2(b). In each profile, the first peak comes from the backscattered light from the turbid medium. The second peak in each profile comes from the backscattered light from the target that is located inside of the turbid medium.

The profile in FIG. 2(a) shows that the backscattered light from the turbid medium and the target is dominated by copolarized light (indicated by the solid curve) for incident linearly polarized light. For circularly polarized light, the backscattered light from the large particle suspensions (turbid medium) is mainly contributed from a single or a few scattering events in large angles, which prefer opposite helicity. Helicity is mostly reversed in the backscattered light similar to results obtained from specular reflection by a mirror. When large particle suspensions are illuminated with input left-handed circularly polarized light, FIG. 2(b) shows that the dominated backscattered light from the host medium (large particle suspensions) has the same handedness as the incident light (indicated by the solid curve). This polarization memory comes from a sequence of smooth forward propagation trajectories that the incident light has experienced before contributing to the backscattered light. The circular polarization decays much slower than the linear polarization after those forward trajectories. Depending on the depolarization properties of the target, the backscattered light from the target is dominated by the light with the opposite helicity. As described below, this observation permits an imaging method that offers improved contrast for targets in a turbid medium to be provided in accordance with the present invention.

In accordance with the present invention, polarization memory of circular polarization provides an effective method for improving imaging of a deep target since the target information and the strong backscattering background light have different helicity. These results indicate that continuous or time-resolved imaging with the cross-polarized backscattered light of the incident circularly polarized light greatly improves the contrast of the image over copolarized backscattered light or total intensity. However, linear polarization imaging has the associated disadvantage that the major target information and strong backscattering light background have the same polarization. Thus, in accordance with the present invention, the employment of an imaging method or technique that utilizes opposite helicity provides improved imaging due to the cross-polarized light.

Figure 3:
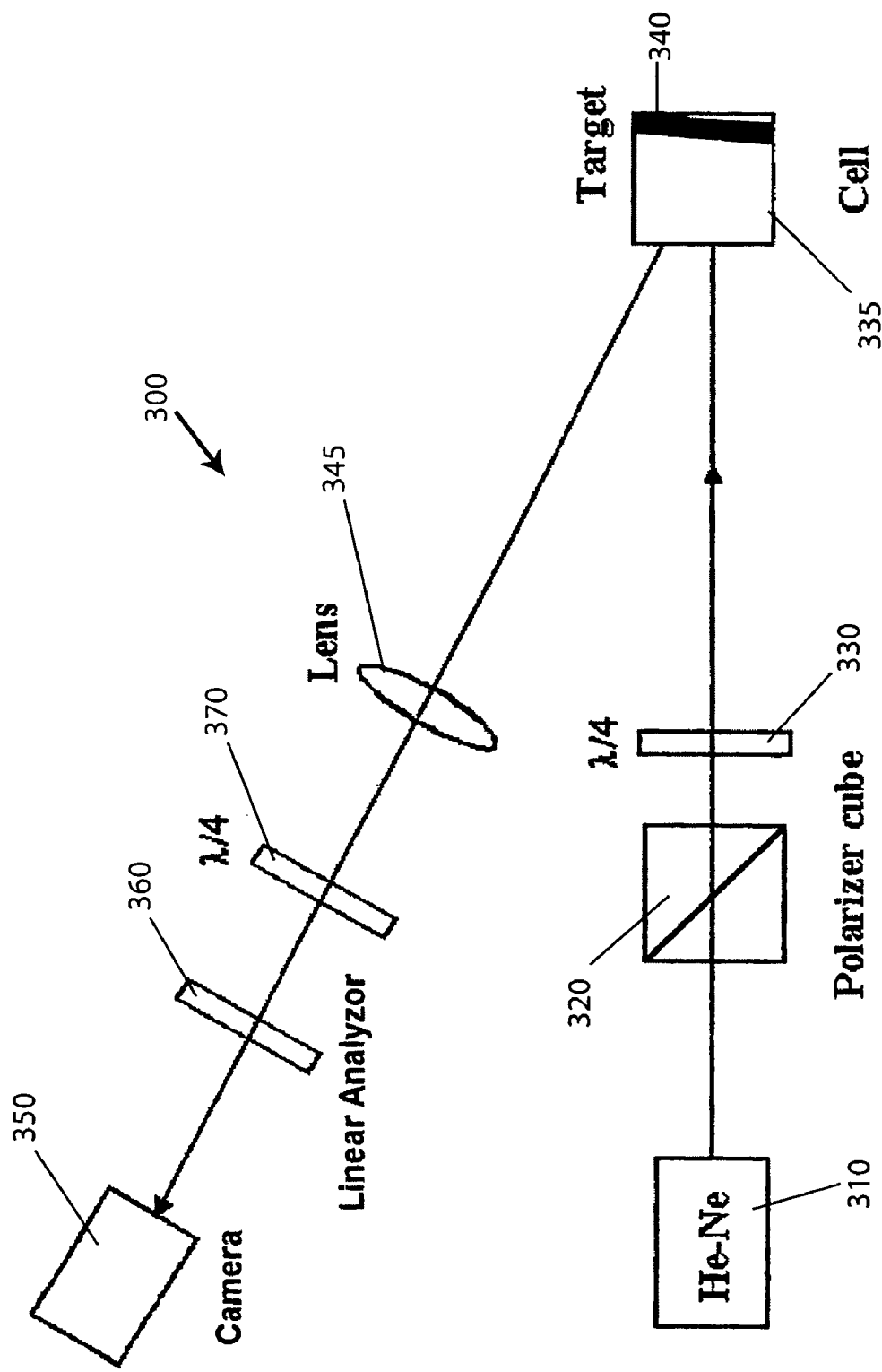
FIG. 3 is a schematic diagram of a backscattering imaging system in accordance with one exemplary embodiment of the present invention.

FIG. 3 is diagrammatic view of one exemplary backscattering imaging system 300 that is configured to provide imaging with improved contrast of a target in a turbid medium. A light source 310 is provided and can be in the form of a laser, such as a He—Ne laser 310, or any other apparatus that can controllably generate light pulses or a light beam. The He—Ne laser light beam first passes through a polarizer 320, such as a cubic polarizer, and then a quarter-wave plate 330 to ensure either linear or circular polarization for the incident light.

The polarized light illuminates a sample (cell) 335 with a target 340 (e.g., a 1951 USAF glass slide positive resolution target) that is disposed inside the turbid medium. It will be understood that the target 340 can be any number of different objects of which imaging is of interest. Thus, the arrangement of FIG. 3 is merely exemplary in nature to illustrate the basic principles of the imaging method of the present invention.

A lens 345 positioned approximately 4° off the backscattering direction is used to image the target 340 to a detector 350 which in this case is configured to record images as opposed to a photodiode type device and in one embodiment, the detector 350 is a CCD camera. Between the lens 345 and the detector 350, a linear analyzer 360 and a quarter-wave plate 370 are provided, with the linear analyzer 360 being optically closer to the detector 350 and the quarter-wave plate 370 is optically closer to the lens 345. The linear analyzer 360 and the quarter-wave plate 370 are provided prior to the detector 350 such that the backscattered light passes through these two elements 360, 370 before impinging the detector 350 for selecting out the linearly or circularly backscattered light.

FIG. 4 shows intensity profiles on a detector (e.g., CCD camera 350) of a highly reflective target inside a turbid medium that consists of large particles that have a diameter a of about 10.143 µm. However, it will be understood the CCD camera 350 is capable of digitizing, storing and displaying actual images of the target and surrounding environment.

FIG. 4(a) shows profiles obtained with linearly copolarized light, while FIG. 4(b) shows profiles with circularly cross-polarized light. The curves represent the intensity profile along a window crossing the middle of the image (the distances across the x-axis represent a distance along the sample window from one edge of the window). The contrast can be obtained from the difference between the maximum intensity of the central bar of the target and minimum intensity for the left background divided by their sum. A significant enhancement of the image contrast is observed for the image with circularly cross-polarized light for the reasons set forth above and in accordance with the teachings of the present invention. The target is located 8.4 mfp's (mean free paths) from the surface and the contrast of image with linearly copolarized light is equal to 0.03 in comparison with 0.1 for circularly cross-polarized light. The polarization memory of the diffusive backscattered circularly polarized light leads to this improvement in contrast since the circular cross-polarized light offers improved imaging contrast compared to the use of linear polorized light.

In accordance with the present invention, the above described imaging techniques and methods can be implemented in any number of different applications, as well as a number of different imaging devices, systems and arrangements, where it is desirable to perform imaging of an object that is present in a turbid medium. For example, this type of imaging through a turbid medium finds particular utility in a number of different medical applications where it is difficult to image target tissue or the like due to the presence of blood, other obscuring fleshy tissue, etc.

It will be appreciated that the size of the particles that are contained within the turbid medium is relative to the wavelength of the light and as the particle size approaches the size of the target, the light is reflected and refracted by the particles instead of scattered by the particle. Thus, imaging based on the above described polarization memory effect is optimized for turbid media where the particle size is greater than the wavelength of the light but the particle size is less than the size of the target. For example and according to one embodiment, the particle size ranges from about 1 to about 20 times the wavelength of the light; however, this range is merely illustrative and is not limiting of the present invention since, in some embodiments, values outside this range may be suitable for providing imaging with sufficient contrast. According to one aspect of the present invention, one exemplary and preferred wavelength for small absorption in blood and tissue is in near infrared from 0.8 µm to about 1.4 µm, e.g., about 1.3 µm, from an LED and semiconductor laser.

Now referring to FIG. 5, in one particular embodiment, an imaging system and method according to another aspect of the present invention is implemented into an intravascular imaging system 400 which can be configured to image an artery wall through a blood field which represents a turbid medium. In this exemplary embodiment, the imaging system 400 includes a light source 410 which can be any number of different types of light sources or devices that generate light having certain prescribed characteristics and properties. For example, the light source 410 can be in the form of a laser or the like that generates light (laser pulses) that is emitted in a first direction. The emitted light is then redirected by means of a first mirror 420 that in the illustrated embodiment is angled to redirect the light at about a 90 degree angle so that the light is introduced to a polarizer 430 which serves to linearly polarize the light that is used for illumination of the artery wall.

After the light passes through the polarizer 430 and is linearly polarized, it then contacts a beam splitter 440 that redirects the light again (e.g., at a 90 degree angle so that it is parallel to initial illumination direction) and the light is directed to a quarter-wave plate 450 that acts to convert the linearly polarized light into circularly polarized light. The circularly polarized light is then delivered via a delivery device, generally indicated at 460, to a blood vessel.

In the illustrated embodiment, the delivery device 460 includes an elongated optical carrier 462 that can carry the illuminated light to the target location and a medical instrument 464 or the like that can be positioned at the target location for illuminating the target. When the target location is inside an artery, the optical carrier 462 has a high degree of flexibility to permit bending thereof to accommodate routing of the carrier 462 through an incision (tissue, etc.) and into the blood vessel itself. For example, the optical carrier 462 can be in the form of an optical fiber or other light carrying fiber and the medical instrument 464 is in the form of a controllable probe, catheter or the like that complements and incorporates the optical carrier 462 to permit a select target, such as an artery wall, to be illuminated.

It will be appreciated that there are a number of different types of optical carriers (optical fibers) 462 that can be used in the system 400 depending in part upon the type of detector that is being used and based upon whether the user wishes to have actual images displayed or whether intensity profiles, such as FIGS. 2a and 2b, are sufficient. Thus, when the detector is merely a photodetector that converts an optical signal to an electrical signal and permits time dependent intensity profiles to be displayed, the optical fiber is of one type; however, if it is desired to record and be able to store actual images using a CCD camera or the like, the optical fiber must be of a type that can support such a detector.

More specifically, the medical instrument 464 can be in the form of an optical catheter that is integrated with a fiber-optic probe and is operatively connected to a motor controller 466 that is configured to manipulate the rotation and translation of the fiber-optic probe based on inputs, such as data or commands entered by the operator or by manual manipulation by the operator of a member associated with the controller 466. In this manner, the operator can position the optical catheter 464 at the target location, such as a spot along the artery wall, for imaging thereof by illuminating the target. Preferably, the catheter 464 can be moved along the entire target area and surrounding areas, in this case, it is moved a distance along the length of the artery and can be rotated as well within the artery.

The target, in this case the artery wall, is illuminated with circularly polarized light and the backscattered light (circularly polarized backscattered light) is collected via the fiber-optic probe (instrument 464). In other words, the backscattered light is collected by the instrument 464 and it travels along the optical carrier 462 and then passes through the quarter-wave plate 450 which once again results in the backscattered circularly polarized light being converted to linearly polarized light.

The detection and analysis of the backscattered light is performed by any number of different means and in particular and according to one exemplary embodiment, an analyzer 470 is provided prior to the backscattered light being delivered to a detector or the like 480. The analyzer 470 is configured to select out (filter) the backscattered light that is perpendicular to the incident polarization (the analyzer 470 thus functions in same manner as the prism in FIG. 1). As with the detector 210, the detector 480 can take any number of different forms. For example, the detector 480 can be in the form of a camera that records the time-resolved profiles of the backscattered light and in one embodiment, the camera 480 is a Hamamatsu 2 ps streak camera which permits information such as that present in FIG. 2b to be collected and displayed. It will thus be understood that when using this type of camera (which acts more as a photodetector), actual imaging of the target is not provided; however, as explained above, the detector 480 is not limited to being of a photodetector type and instead can be in the form of a detector that is configured to provide images. For example, the detector 480 can be a CCD camera that can record images and in which case, the optical fibers 462 are of the type that collects the backscattered light and permits processing of it by the CCD camera 480 into images that can be displayed. Such optical fibers can be provided as a bundle in the catheter 464.

In the exemplary embodiment illustrated in FIG. 5, the system 400 is arranged and configured so that parallel polarized light is converted to right-handed circularly polarized light (RH) after passing through the polarizer 430 and the quarter-wave plate 450. The backscattered light, which is formed when the light passing through the optical probe illuminates the target, in this case, the artery wall, is a mixture of left-handed circularly polarized light (LH) and right-handed circularly polarized light which is collected by the optical probe and then delivered back to quarter-wave plate 450 through the optical fiber 462. After passing through the quarter-wave plate 450, the right-handed circularly polarized light is converted to parallel polarized light and the left-handed circularly polarized light is converted to perpendicular polarized light. The analyzer 470 is oriented perpendicular to the polarizer 430 and is therefore constructed to select out the perpendicular light for detection by the detector 480. It will be appreciated that various elements of the system 400 can be changed so as to influence the characteristics of the polarized light and the above description is merely one example of an imaging system that employs circular polarized light for achieving imaging with improved resolution in turbid medium settings.

Once again, the handedness of the circular polarized light that is used to illuminate the target and the type that is selected out by a device before the detector is not critical so long as the backscattered light that is selected out is of the opposite helicity relative to the incident light.

FIG. 6 is an enlarged cross-sectional view of the instrument 464 (optical catheter/fiber optic probe) disposed within an artery between the artery wall. More specifically, FIG. 6 shows the light migration of circularly polarized light (e.g., right-handed circularly polarized light) that is used to illuminate the artery wall through a blood field that represents a turbid medium since it includes blood particles, etc., that act as an impediment to conventional imaging techniques. The backscattered light from the artery wall is dominated by left-handed circularly polarized light. In contrast, the backscattered light from the particles contribute mostly right-handed circularly polarized light to the fiber optic probe as shown in FIG. 6. A mixture of left-handed and right-handed circularly polarized light is delivered back to the imaging system 400 and in particular, is delivered to the analyzer 470 for selecting out circular polarized light of one handedness.

It will also be appreciated that the analyzer that is located before the detector or CCD camera can be parallel or perpendicular to the incident linear polarization to select out the helicity reversed photon depending on the alignment of the quarter waveplate. It is also possible to use a circular analyzer instead of the quarter waveplate and linear polarizer before the detector to select out the helicity reversed photon. Moreover, a circular polarizer can be used instead of a linear polarizer plus the quarter waveplate for generating the incident circular polarized light.

FIG. 7 is a schematic diagram of a system 500 for imaging a target, such as an artery wall, using circular polarization memory, according to the present invention, in combination with other methods, such as optical coherence tomography (OCT), Raman, fluorescence, scattering, absorption and emission methods (generally indicated at 510). Using circularly polarized light, the image contrast of those methods can be further improved for the reasons discussed above.

From the foregoing description it can be seen that the present invention is directed to an imaging technique or method that can substantially improve the image contrast of target inside large particle suspensions. This technique has a potential application in medical and atmospheric environment imaging since heavy ground fog, light rain, smoke, biological tissue and blood contain large particles with large anisotropy factor (g) that closely resemble parameters discussed above.

The embodiments of the present invention recited herein are intended to be merely exemplary and those skilled in the art will be able to make numerous variations and modifications to it without departing from the spirit of the present invention. All such variations and modifications are intended to be within the scope of the present invention as defined by the claims appended hereto.

What is claimed:

1. A method for analyzing an object located in a turbid medium comprising the steps of:
   illuminating the object through the turbid medium with circularly polarized light such that backscattered light emerges from the illuminated turbid medium;
   passing the backscattered light through a first device to select out backscattered light that has an opposite helicity relative to the incident polarization; and
   detecting the backscattered light with opposite helicity that passes through the first device to permit detection of the object;
   wherein particles within the turbid medium have a dimension (a) that is greater than the wavelength ($\lambda$) of the backscattered light.

2. The method as claimed in claim 1, wherein the first device is selected from the group consisting of (a) a retardation $\lambda/4$ plate and a linear polarizer and (b) a circular polarizer.

3. The method as claimed in claim 1, wherein the step of detecting the backscattered light is performed over an area using a detector selected from the group consisting of:
   a photomultiplier, a photodiode, a CCD camera, and a photodetector to permit at least one of an light intensity profile or an image of the object to be achieved.

4. The method as claimed in claim 1, wherein the step of detecting the backscattered light is performed point-by-point using one of a photomultiplier, a photodiode and a photodetector.

5. The method as claimed in claim 1, wherein the polarized backscattered light that emerges from the turbid medium has a wavelength that exhibits minimum absorption in turbid medium.

6. The method as claimed in claim 1, wherein the turbid medium is a tissue sample.

7. The method as claimed in claim 6, wherein the tissue sample is a human tissue sample.

8. The method as claimed in claim 7, wherein the human tissue sample is selected from the group consisting of human breast tissue, human brain tissue, human prostate tissue, human liver tissue, human skin tissue, human gastrointestinal tissue, human mucosa tissue, human GYN tissue, human under-arm glandular tissue, human kidney tissue and cells in tissues.

9. The method as claimed in claim 1, wherein the turbid medium is an atmospheric environment.

10. The method as claimed in claim 9, wherein the atmospheric environment comprises one of aerosols, heavy fog, and cumulus conditions.

11. The method as claimed in claim 1, wherein the turbid medium is surgical smoke generated during performance of a surgical operation.

12. The method of claim 1, wherein the dimension (a) of the particles is from about 1 to about 20 times the wavelength ($\lambda$).

13. The method of claim 1, further including the step of:
    processing the detected backscattered light with opposite helicity to provide a displayable image of the target.

14. A method for analyzing coronary lesions, such as vulnerable plaques inside the walls of the arteries, comprising the steps of:
    directing near-infrared circularly polarized light onto a target blood vessel with an optical instrument;
    illuminating a wall of the vessel that contains blood flow;
    detecting backscattered light from the artery wall and from objects within the blood vessel, the detected backscattered light having an opposite helicity relative to incident polarization; and analyzing the backscattered light with opposite helicity from the artery.

15. The method as claimed in claim 14, wherein the step of detecting the backscattered light is performed over an area using one of a photomultiplier, a photodiode, a CCD camera and a photodetector to determine and locate plaque.

16. The method as claimed in claim 14, wherein the step of detecting the backscattered light is performed point-by-point using one of a photomultiplier, a photodiode and a photodetector.

17. A method as claimed in claim 14, wherein a surface of the artery wall is imaged through a blood field using circularly polarized light of opposite helicity with a wavelength less than 1 µm.

18. The method as claimed in claim 14, further including the step of:
    imaging the wall of artery for plaque by at least one optical method selected from the group consisting of OCT, Raman, fluorescence, absorption, scattering, or emission.

19. The method as claimed in claim 14, wherein the step of analyzing the backscattered light with opposite helicity from the artery includes the steps of:
    directing the backscatter light opposite helicity to a detector;
    processing the detected backscattered light with opposite helicity by means of the detector to provide a displayable image of the target.

20. An optical system for imaging a target located within a suspension of scattering particles that at least in part define a turbid medium comprising:
    a light source producing parallel polarized light;
    a first device for converting the parallel polarized light to circularly polarized light having a first handedness;
    an optical instrument that illuminates the target with the circularly polarized light resulting in backscattered light being formed that comprises circularly polarized light having the first handedness and circularly polarized light having an opposite second handedness which are collected by a probe of the instrument;
    a second device for converting the circularly polarized light having the first handedness into parallel polarized light and the circularly polarized light having the second handedness into perpendicular polarized light; and
    a third device that is configured to select out the perpendicular polarized light for detection by a detector that is configured to process the perpendicular polarized light and provide displayable information concerning the target;
    wherein a dimension of the scattering particles is greater than a wavelength ($\lambda$) of the circularly polarized backscattered light.

21. The system of claim 20, wherein the circularly polarized light having a first handedness comprises right-handed circularly polarized light and the circularly polarized light having a second handedness comprises left-handed circularly polarized light.

22. The system of claim 20, wherein the light source comprises a laser.

23. The system of claim 20, wherein the optical instrument comprises an optical catheter that is communication with the first and second polarizing devices via a flexible optical carrier and the probe is a fiber optic probe integrated with the catheter.

24. The system of claim 20, wherein the first device comprises a first polarizer and a quarter-wave plate that is located optically downstream from the first polarizer.

25. The system of claim 20, wherein the second device includes a quarter-wave plate.

26. The system of claim 20, wherein the third device comprises an analyzer that is located perpendicular to a first polarizer that is part of the first device.

27. The system of claim 20, wherein the detector is device that is selected from the group consisting of a photomultiplier, a photodiode, a CCD camera and a photodetector.

28. The system of claim 20, wherein the detector is a CCD camera that is configured to process the perpendicular polarized light and provide a displayable image of the target.

29. The system of claim 20, wherein the dimension of the scattering particles is a diameter of the particles and the diameter is in a range from about 1 to about 20 times the wavelength of the light.

30. The system of claim 20, the wavelength ($\lambda$) is from about 0.8 μm to about 1.4 μm.

31. The system of claim 20, wherein the target comprises plaque that is present along an artery wall and the scattering particles includes blood particles.

32. A system for imaging a target that is located within a turbid medium that is defined in part by a suspension of scattering elements that have a dimension (a) comprising:
   a light source producing polarized light;
   a first device for converting the polarized light to circularly polarized light;
   an instrument operatively and optically connected to the light source and configured to illuminate the element with the circularly polarized light and to collect circularly polarized backscattered light that is formed;
   a second device for converting the circularly polarized backscattered light into copolarized light and cross-polarized light relative to the polarized light of the light source;
   a third device for filtering out the cross-polarized light from the copolarized light; and
   a fourth device for receiving and processing the filtered cross-polarized light and record graphic images of the target, wherein the filtered cross-polarized light has a wavelength ($\lambda$) less than the dimension (a) of the scattering elements.

33. The system of claim 32, wherein the instrument is constructed and dimensioned to be received within a blood vessel.

34. The system of claim 32, wherein the light source generates parallel polarized light and the coplanarized light is parallel polarized light, while the cross-polarized light is perpendicular polarized light.

35. The system of claim 32, wherein the first device generates right-handed circularly polarized light and the backscattered light comprises both right-handed circularly polarized light and left-handed circularly polarized light that is converted to perpendicular polarized light by the second device.

36. The system of claim 33, wherein the instrument comprises an optical catheter that is communication with the first and second devices via a flexible optical carrier and includes a fiber optic probe integrated with the catheter that collects the backscattered light and supports the fourth device so that a graphic image of the target can be displayed.

37. The system of claim 32, wherein the first device comprises a first polarizer and a quarter-wave plate that is located optically downstream from the first polarizer.

38. The system of claim 32, wherein the second device comprises a quarter-wave plate.

39. The system of claim 32, wherein the third device comprises an analyzer that is located perpendicular to a first polarizer that is part of the first device.

* * * * *